(12) United States Patent
Bayer

(10) Patent No.: US 9,952,018 B2
(45) Date of Patent: Apr. 24, 2018

(54) DEVICE FOR EVENT REPRESENTATIONS IN DUEL SHOOTING

(71) Applicant: Reiner Bayer, Trippstadt (DE)

(72) Inventor: Reiner Bayer, Trippstadt (DE)

( * ) Notice: Subject to any disclaimer, the term of this patent is extended or adjusted under 35 U.S.C. 154(b) by 0 days.

(21) Appl. No.: 15/302,233

(22) PCT Filed: Apr. 15, 2015

(86) PCT No.: PCT/DE2015/100158
§ 371 (c)(1),
(2) Date: Oct. 6, 2016

(87) PCT Pub. No.: WO2015/158332
PCT Pub. Date: Oct. 22, 2015

(65) Prior Publication Data
US 2017/0023331 A1    Jan. 26, 2017

(30) Foreign Application Priority Data
Apr. 15, 2014 (DE) .................... 20 2014 101 791 U

(51) Int. Cl.
*F41G 3/26* (2006.01)
*A61F 11/14* (2006.01)
(Continued)

(52) U.S. Cl.
CPC ................ *F41G 3/26* (2013.01); *A61F 11/14* (2013.01); *F41A 35/00* (2013.01); *F41C 27/00* (2013.01); *F41G 1/46* (2013.01); *F41J 7/06* (2013.01); *F41J 11/00* (2013.01); *G02B 27/017* (2013.01); *G02B 27/0189* (2013.01)

(58) Field of Classification Search
CPC ... F41G 3/26; F41G 3/00; F41A 33/00; F41A 35/00; A61F 11/14; F41J 7/06; F41J 5/10; G02B 27/017; G02B 27/0189; G09G 5/00
See application file for complete search history.

(56) References Cited

U.S. PATENT DOCUMENTS 5,353,134 A * 10/1994 Michel .................... F41G 3/165
                                                                    33/262
8,955,749 B2 * 2/2015 Elefante .................... F41G 3/16
                                                                    235/404
(Continued)

FOREIGN PATENT DOCUMENTS

DE      74 40 222 U1    3/1975
DE      40 31 937 A1    4/1992
(Continued)

OTHER PUBLICATIONS

International Search Report of PCT/DE2015/100158, dated Jul. 10, 2015.

*Primary Examiner* — Benjamin P Lee
(74) *Attorney, Agent, or Firm* — Collard & Roe, P.C.

(57) ABSTRACT

The invention relates to a device for event representation in duel shooting.
Known devices have the disadvantage that, in order to practice duel shooting, it is always necessary to modify a shooting range.
The aim of the invention is to create a device for duel shooting which does not require complicated modification of a shooting range.
This aim is achieved according to the invention in that a visualizing unit is provided for representing events, which is positionable within the range of perception of the marksman's eye.

7 Claims, 2 Drawing Sheets

(51) Int. Cl.
  *G02B 27/01* (2006.01)
  *F41J 7/06* (2006.01)
  *F41J 11/00* (2009.01)
  *F41A 35/00* (2006.01)
  *F41G 1/46* (2006.01)
  *F41C 27/00* (2006.01)

(56) References Cited

U.S. PATENT DOCUMENTS

| | | | | |
|---|---|---|---|---|
| 8,964,298 B2* | 2/2015 | Haddick | ............... | G06F 3/013 |
| | | | | 359/630 |
| 9,116,340 B2* | 8/2015 | Jacobsen | ............... | G02B 27/017 |
| 9,310,613 B2* | 4/2016 | Jacobsen | ............... | G02B 27/017 |
| 9,344,612 B2* | 5/2016 | Ritchey | ............... | H04N 5/2254 |
| 2006/0221266 A1* | 10/2006 | Kato | ............... | G02B 27/017 |
| | | | | 348/838 |
| 2009/0146916 A1 | 6/2009 | Moliton | | |
| 2010/0238161 A1* | 9/2010 | Varga | ............... | G06T 17/05 |
| | | | | 345/419 |
| 2010/0302282 A1* | 12/2010 | Dobbie | ............... | F41G 1/35 |
| | | | | 345/666 |
| 2011/0001699 A1* | 1/2011 | Jacobsen | ............... | G06F 3/012 |
| | | | | 345/157 |
| 2012/0075168 A1* | 3/2012 | Osterhout | ............... | G02B 27/017 |
| | | | | 345/8 |
| 2012/0274922 A1* | 11/2012 | Hodge | ............... | F41J 5/02 |
| | | | | 356/28 |
| 2014/0092245 A1 | 4/2014 | Moore et al. | | |
| 2014/0123535 A1* | 5/2014 | Thomas | ............... | F41G 1/40 |
| | | | | 42/122 |
| 2014/0240313 A1* | 8/2014 | Varga | ............... | G06T 19/006 |
| | | | | 345/419 |
| 2014/0368412 A1* | 12/2014 | Jacobsen | ............... | G02B 27/017 |
| | | | | 345/8 |
| 2015/0130839 A1* | 5/2015 | Kasahara | ............... | G06T 7/60 |
| | | | | 345/633 |
| 2015/0253109 A1* | 9/2015 | Wichner | ............... | F41A 17/12 |
| | | | | 434/19 |
| 2016/0069643 A1* | 3/2016 | Lyren | ............... | G09B 19/0038 |
| | | | | 345/589 |
| 2016/0209648 A1* | 7/2016 | Haddick | ............... | G02B 27/0093 |

FOREIGN PATENT DOCUMENTS

| | | |
|---|---|---|
| DE | 20 2009 014 784 U1 | 12/2010 |
| DE | 20 2011 102 282 U1 | 12/2011 |
| EP | 0 669 512 A1 | 8/1995 |
| WO | 2009/135674 A1 | 11/2009 |

* cited by examiner

FIG. 3
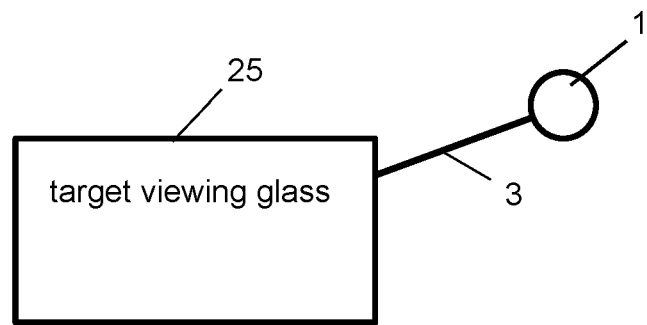
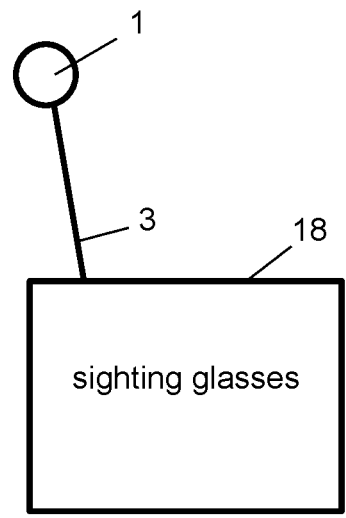
FIG. 4

DEVICE FOR EVENT REPRESENTATIONS IN DUEL SHOOTING

CROSS REFERENCE TO RELATED APPLICATIONS

This application is the National Stage of PCT/DE2015/100158 filed on Apr. 15, 2015, which claims priority under 35 U.S.C. § 119 of German Application No. 20 2014 101 791.7 filed on Apr. 15, 2014, the disclosure of which is incorporated by reference. The international application under PCT article 21(2) was not published in English.

BACKGROUND OF THE INVENTION

1. Field of the Invention

The invention relates to a device for event representation in duel shooting.

2. Description of the Related Art

The DE 74 40 222 U1 describes an air pistol range with a pull cable which is guided over deflection pulleys and to which, between the firing point and the backstop, a movable carrier having holding means for a precision target is attached, said holding means additionally being configured to hold a duel-shooting target and being mounted on the carrier via an electrically powered rotary member that can be swiveled between a firing position with a visible rotatable target and a rest position in which the target has been swiveled out of the field of view.

The DE 40 31 937 A1, too, describes a shooting range with a single target. It is particularly suitable for competitive duel shooting with air guns and is mounted on the carriage of a target traction system such as to be rotatable about a vertical axis. The electric motor is controllable, via a microprocessor and a wireless remote control, in such a way that the target carries out the 90° rotary movement required for duel shooting at pre-defined intervals.

The DE 20 2011 102 282 U1 discloses a duel shooting setup comprising at least two firing devices, each of which has a source of electromagnetic rays and at least two target setups, each of the latter having at least one photodetector for detecting electromagnetic rays from the firing-device sources and a signal device connected to the photodetector via a resettable switch, the switches being interconnected in such a way that on detection of electromagnetic rays by a photodetector a signal device is activated and the detection is perceivable as the first hit. The signal device is positioned in the centre of the target.

These devices have the disadvantage that, in order to practice duel shooting, it is always necessary to modify a shooting range.

SUMMARY OF THE INVENTION

The aim of the invention is to create a device for duel shooting which does not require complicated modification of a shooting range.

This aim is achieved according to the invention in that a visualizing unit is provided for event representation, which is fastenable to a piece of equipment positioned in the immediate vicinity of the marksman during firing and via which an event can be represented within the range of perception of the marksman's eye.

Surprisingly, it became apparent within the framework of the invention that it suffices to position a visualizing unit within the range of preception of the marksman's eye in order to indicate the firing period to the marksman. It is important in this context that the visualizing unit is not positioned in the area between the eye and the target. This would interfere with aiming. It suffices fully to position the visualizing unit such that it is still just within the field of vision of the marksman's eye or is projected as bundled light (laser) directly onto a region of the target. The firing period may be indicated to the marksman by a change in colour or brightness or some other signal from the visualizing unit. The advantage of this device is that the shooting range requires no modifications and that it is also possible to practice aiming outside of shooting ranges, for example at the marksman's home. Practice in the periodically alternating process, so important in duel shooting, of aiming during a firing period and then waiting, can be had with a device of this kind.

The visualizing unit may be fastened to a piece of equipment positioned in the immediate vicinity of the marksman during firing, for example to the marksman's target viewing glass or hearing protector.

This embodiment of the invention is inexpensive to realise since duel shooting requires the wearing of a hearing protector, making it possible to position the visualizing unit within the marksman's range of vision. The power supply and the digital electronics may be accommodated in the area of the hearing protector. The same applies to other pieces of equipment, such as the target viewing glass.

It is advantageous in this context for the hearing protector to have a socket into which a plug of the visualizing unit can be inserted.

The hearing protector may then simply be provided with a visualizing unit for duel shooting. When no longer required, it is simply removed from the hearing protector.

It is also useful in this context to mount the visualizing unit on a flexible support element.

The flexible support element may be, for example, a flexible rod of the kind used with microphones. This enables the visualizing unit to be adapted to the particular marksman's physiognomy. The plug for connecting the visualizing unit to the socket in the ear protector may be positioned at the opposite end of the flexible support element to the visualizing unit.

Another preferred embodiment of the invention consists in that the visualizing unit is fastenable to shooting glasses.

Shooting glasses, too, are often worn for duel shooting. It is accordingly possible to fasten the visualizing unit to a marksman's shooting glasses, for example to the cover. Here too, the visualizing unit is not positioned in the area between the eye and the target but just within the eye's field of vision.

It is within the scope of the invention for the visualizing unit to be provided additionally with an acoustic signal transmitter.

This acoustic signal transmitter may signalize the firing period and the waiting times to the marksman, supplementing the optical signal from the visualizing unit. This is particularly easy to realize if the visualizing unit is plugged into the marksman's hearing protector.

A refinement of the invention consists ultimately in that a microphone and evaluating electronics are integrated in the visualizing unit.

The dispensed shot may be registered with a microphone of this kind and the length of time between commencement of the particular firing period and firing of the shot determined with the evaluating electronics. If targets with electronic hit detection are used, the signal-transmitting electronics may be coupled with the evaluating electronics of the relevant shooting range.

BRIEF DESCRIPTION OF THE DRAWINGS

An embodiment of the invention is explained below by reference to drawings.

The drawing in

FIG. 3 shows a target viewing glass with the visualizing unit fastened thereto; and FIG. 4 shows sighting glasses with a visualizing unit fastened thereto.

DETAILED DESCRIPTION OF THE PREFERRED EMBODIMENTS

Figure 1:
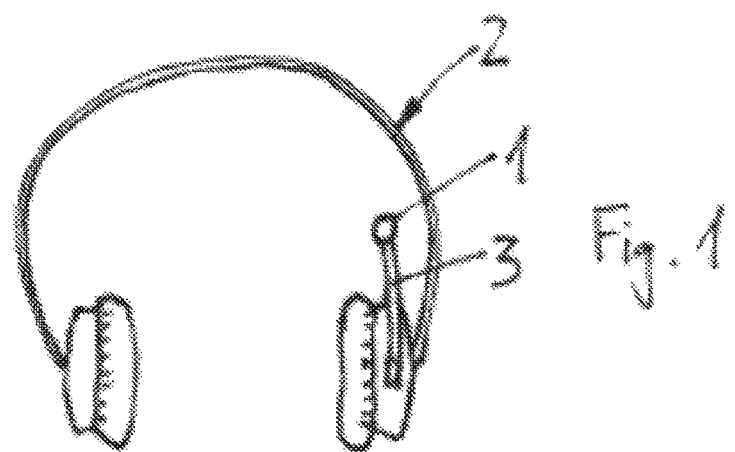
FIG. 1 shows a visualizing unit according to the invention, attached to a hearing protector.

As shown in FIG. 1, a visualizing unit 1 is fastened to a hearing protector 2 for a marksman. In order to adapt the visualizing unit 1 to the physiognomy of the marksman in question, the visualizing unit is mounted on a flexible support element 3, thereby enabling the marksman to position the visualizing element 1 to suit his personal requirements.

Figure 2:
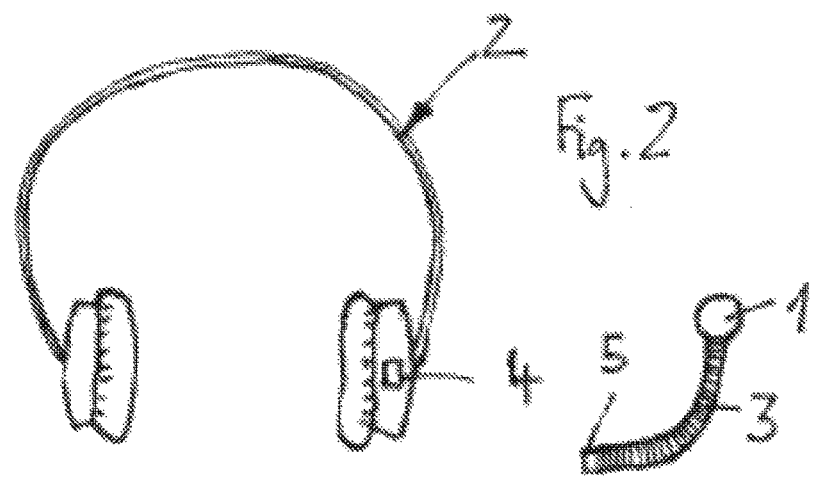
FIG. 2 shows the hearing protector with the visualizing unit detached.

FIG. 2 shows the hearing protector with the visualizing unit detached, with the latter shown in enlarged form.

In the embodiment described here, the hearing protector 2 has a socket 4 into which a plug 5 at the opposite end of the flexible support element 3 to the visualizing unit 1 can be inserted. The electrical power supply and the digital electronics for the visualizing unit 1, and maybe a supplementary acoustic signal transmitter, may be located in the area of the hearing protector 2. Finally, a microphone and evaluating electronics may be accommodated in the hearing protector.

If the marksman wishes to practice duel shooting, he inserts the plug 5 of the visualizing unit 1 into the socket 4 of the hearing protector 2, positions the visualizing unit 1 such that it is still just in his field of vision and switches on the visualizing unit 1, for example by way of a remote control or a switch in the vicinity of the hearing protector 2. The visualizing unit 1 then signalizes the firing periods and the waiting times by means of brightness changes, colour signals or other signals—possibly supplemented by a simultaneous acoustic signal. The dispensed shot is detected via the microphone and the time between commencement of the firing period and firing of the shot determined by means of the evaluating electronics.

The duel practicing unit is thus installed and operated in the immediate vicinity of the marksman, enabling him to practice duel shooting at any time and at any desired shooting range without disturbing another marksman standing beside him.

FIG. 3 shows a target viewing glass 25 with the visualizing unit 1 fastened thereto via a fastener 3.

FIG. 4 shows sighting glasses 18 with a visualizing unit 1 fastened thereto via a fastener 3.

The invention claimed is:

1. A device for representing shooting periods and waiting times in duel shooting,
    wherein a visualizing unit is provided for representing the shooting periods and the waiting times,
    wherein the visualizing unit is fastenable to a piece of equipment in the immediate vicinity of the marksman during firing, but not positioned between the marksman's eye and the target,
    wherein the visualizing unit is configured to represent the shooting periods and the waiting times within the range of perception of the marksman's eye,
    wherein a microphone and evaluating electronics are integrated in the visualizing unit,
    wherein the microphone is configured to detect the shot dispensed, and
    wherein the evaluating electronics are configured to determine the time between commencement of the shooting period and firing of the shot.

2. The device according to claim 1, wherein the piece of equipment is a target viewing glass.

3. The device according to claim 1, wherein the piece of equipment is a hearing protector worn by the marksman.

4. The device according to claim 3, wherein the marksman's hearing protector has a socket into which a plug of the visualizing unit can be inserted.

5. The device according to claim 1, wherein the visualizing unit is mounted on a flexible support element.

6. The device according to claim 1, wherein the visualizing unit can be fastened to shooting glasses.

7. The device according to claim 1, wherein the visualizing unit is provided additionally with an acoustic signal transmitter.

* * * * *